United States Patent [19]

Gross

[11] Patent Number: 4,587,849
[45] Date of Patent: May 13, 1986

[54] COEXTRUSION INSPECTION SYSTEM
[75] Inventor: R. Michael Gross, Muncie, Ind.
[73] Assignee: Ball Corporation, Muncie, Ind.
[21] Appl. No.: 706,689
[22] Filed: Feb. 28, 1985
[51] Int. Cl.⁴ .......................................... G01N 29/04
[52] U.S. Cl. ...................................... 73/644; 73/159
[58] Field of Search ......................... 73/644, 633, 159

[56] References Cited

U.S. PATENT DOCUMENTS

| | | | |
|---|---|---|---|
| 3,121,326 | 2/1964 | Klatchko | 73/644 |
| 3,159,756 | 12/1964 | Beaujard et al. | 310/336 |
| 3,171,047 | 2/1965 | Bergman et al. | 73/644 |
| 3,218,846 | 11/1965 | Joy | 73/644 |
| 3,233,449 | 2/1966 | Harmon | 73/622 |
| 3,255,626 | 6/1966 | Van Der Veer | 73/644 |
| 3,485,088 | 12/1969 | O'Connor | 73/644 |
| 3,631,714 | 1/1972 | Cressman et al. | 73/644 |
| 3,712,119 | 1/1973 | Cross et al. | 73/614 |
| 4,012,946 | 3/1977 | Patsey | 73/644 |
| 4,033,178 | 7/1977 | Holt et al. | 73/644 |
| 4,279,167 | 7/1981 | Erb et al. | 73/861.25 |
| 4,333,352 | 6/1982 | Connery et al. | 73/861.18 |
| 4,410,826 | 10/1983 | Waxman et al. | 310/336 |
| 4,429,577 | 2/1984 | Sorenson et al. | 73/644 |
| 4,435,985 | 3/1984 | Wickramasinghe | 73/642 |
| 4,454,764 | 6/1984 | Sorenson | 73/642 |
| 4,470,307 | 9/1984 | Genter et al. | 73/634 |

*Primary Examiner*—Anthony V. Ciarlante
*Attorney, Agent, or Firm*—Gilbert E. Alberding

[57] ABSTRACT

An ultrasonic inspection apparatus is disclosed for inspecting coextruded plastic sheet as it is produced. The apparatus includes support for the sheet to be inspected and support for an ultrasonic transducer adjacent the surface of said sheet. A housing supports the ultrasonic transducer adjacent the sheet and defines a chamber between the face of the transducer and the surface of the sheet. The chamber is provided with an interfacing fluid so that ultrasonic pulses from the transducer will pass through the fluid into the sheet to be reflected from any interface therein. The ultrasonic transducer and interfacing fluid are moved across the surface of the sheet to permit inspection of the entire sheet. Means are provided within the fluid chamber for directing interfacing fluid substantially transversely across the face of the transducer to remove any air bubbles that may form between the transducer face and the sheet. The ultrasonic pulse echoes received from the sheet may be analyzed to provide an indication of the presence and depth of interfaces in the sheet.

25 Claims, 7 Drawing Figures

COEXTRUSION INSPECTION SYSTEM

BACKGROUND OF THE INVENTION

The present invention relates generally to an acoustic inspection system, and more particularly, to a method and apparatus for ultrasonically inspecting continuous sheets in an on-line production basis.

Ultrasonic transducers are often used to inspect various articles in a non-destructive manner. Typically, these devices include a pulser/receiver which produces an electrical pulse that excites a piezoelectric or magnetostrictive transducer, causing it to emit an ultrasonic pulse. In the "pulse-echo" technique, this ultrasonic pulse travels into the article under inspection until it is reflected from an interface. The reflected pulse is received and converted by the same transducer into an electrical signal which is then amplified and conditioned by the receiver for further analysis. In some applications, the "through-transmission" technique is used where the signal is transmitted by one transducer and received by a second transducer; but the generation and reception of pulses is similar to the "pulse-echo" technique. The transducer output may be analyzed to provide information concerning imperfections in the article, and the results can be displayed on an oscilloscope or other output medium.

Ultrasonic transducers have been used to inspect continuous coextruded plastic sheet in order to detect the presence of a barrier layer therein. In such an application, it is necessary to provide a coupling medium between the face of the transducer and the near surface of the plastic sheet being inspected so that the face of the transducer will not reflect the majority of the ultrasonic energy. One known technique for accomplishing this is to provide a large vat containing an interfacing medium (e.g., water), immersing the face of the transducer in the medium, and then passing the plastic sheet through the medium beneath the transducer.

This technique requires that the portion of the sheet being inspected be fully submerged within the interfacing medium in the vat. The vat requires a substantial amount of space within the manufacturing facility which can usually be put to more effective use. Such inspection systems also frequently require that the sheet be bent or otherwise deformed so that it can be properly submerged in a reasonably sized vat. Bending the sheet is undesirable as this can easily cause the sheet to be damaged.

Ultrasonic transducer apparatus, having means for maintaining a coupling medium between the transducer and the portion of the surface of an article under inspection are also known. In U.S. Pat. No. 3,485,088, for example, an ultrasonic transducer apparatus is described which includes structure for maintaining a column of interfacing fluid between the face of the transducer and the surface of an article being inspected.

A serious problem with many apparatus of this type is that air bubbles tend to become entrapped in the fluid between the face of the transducer and the surface of the article under inspection, particularly, adjacent the face of the transducer. Any air bubbles which are present in this region, even bubbles of microscopic size, can cause substantial error in the accuracy and performance of the measurements.

In using transducer apparatus of this type to inspect extensive articles, it may be desirable to move the transducer apparatus and the article relative to each other to permit different portions of the article to be inspected. When the article being inspected is a coextruded plastic sheet or another article of relatively fragile nature, there is a substantial risk of abrading or otherwise damaging the surface of the article by the transducer apparatus.

SUMMARY OF THE INVENTION

The present invention provides a reliable and accurate acoustic-inspection system and method for ultrasonically inspecting articles such as coextruded plastic sheet in a manner that makes it unnecessary to submerge the sheet in an interfacing medium. The system according to a presently preferred embodiment comprises a support frame or table which carries means such as a plurality of rollers for receiving and supporting a sheet in position to be inspected. The table further includes means for suppporting one or more transducer means in contact with the sheet for inspecting the sheet. Each of the transducer means comprises means for maintaining an interfacing medium such as water or another fluid between the face of the transducer and the surface of the sheet being inspected so that ultrasonic pulses from the transducer will pass through the interfacing medium and into the sheet.

Drive means are coupled to the means for supporting the transducer means to move the transducer means in a predetermined path back and forth across the sheet as the sheet moves in a direction transverse to the direction of movement of the transducer means so that the sheet can be inspected in a systematic manner.

As each of the transducer means moves back and forth across the surface of the sheet, the interfacing medium supported therein moves along with it to maintain the interfacing medium between the face of the ultrasonic transducer and the surface of the portion of the sheet being inspected at all times. Thus, it is unnecessary to completely submerge the sheet in a liquid-filled vat, or to bend or otherwise deform the sheet as in many current systems.

Each transducer means includes a housing supporting an ultrasonic transducer in spaced relationship with respect to an article to be inspected and includes means for defining a chamber for maintaining interfacing fluid between the face of the transducer and the article being inspected. In addition, each transducer means includes means for directing interfacing fluid substantially transversely across the face of the transducer to prevent the entrapment of any air bubbles in the fluid between the face of the transducer and the article.

According to a presently preferred embodiment, the fluid directing means includes a disk-shaped element positioned within the chamber and defining a first chamber portion adjacent the face of the transducer and a second chamber portion adjacent the surface of the article. The element includes a fluid directing surface for directing the fluid within the first chamber portion substantially transversely across the face of the transducer. The disk-shaped element further includes a plurality of peripheral apertures and a central aperture to permit ultrasonic energy to be transmitted from the transducer through the interfacing fluid into the article and back to the transducer.

The housing further includes a fluid inlet connected to a source of interfacing fluid and a fluid outlet, and an annular sleeve is positioned around the ultrasonic transducer and is provided with a first plurality of inlet passageways for directing interfacing fluid into the chamber to be directed across the face of the transducer by the fluid directing means; and a second plurality of outlet passageways for directing interfacing fluid and any air bubbles carried thereby out of the first chamber portion to the fluid outlet. The first plurality of inlet passageways surround a substantial portion of the circumference of the transducer so that the face thereof will be effectively washed clear of air bubbles by fluid flowing thereacross.

In operation, as the transducer means and the article are moved transversely relative to one another during inspection of the article, a fast moving stream of interfacing fluid is maintained across the face of the transducer by the disk-shaped element. Some of the fluid will pass through the central and peripheral apertures in the element into the second chamber portion to replenish fluid lost between the base of the housing and the surface of the article. The remainder of the fluid will exit the first chamber portion through the second plurality of passageways to the fluid outlet. Any air bubbles that may otherwise tend to accumulate within the chamber will thus be carried away from the face of the transducer and will be prevented from affecting the accuracy of the measurements.

The housing is preferably provided with a soft, flexible housing base of urethane elastomer or the like to help reduce fluid leakage from the chamber and to prevent the surface of the article from being abraded or otherwise damaged by the transducer means.

The table also supports the means for analyzing the ultrasonic echoes returned to the transducers. As the transducer means move back and forth across the sheet, they generate ultrasonic pulses which are reflected back to the transducers. The analyzing means analyzes these signals to provide an indication of the presence of various layers including any barrier layer in the coextruded plastic sheet.

Further features of the invention will be set out hereinafter in conjunction with the detailed description of the preferred embodiments.

DETAILED DESCRIPTION OF THE PREFERRED EMBODIMENT

Figure 1:
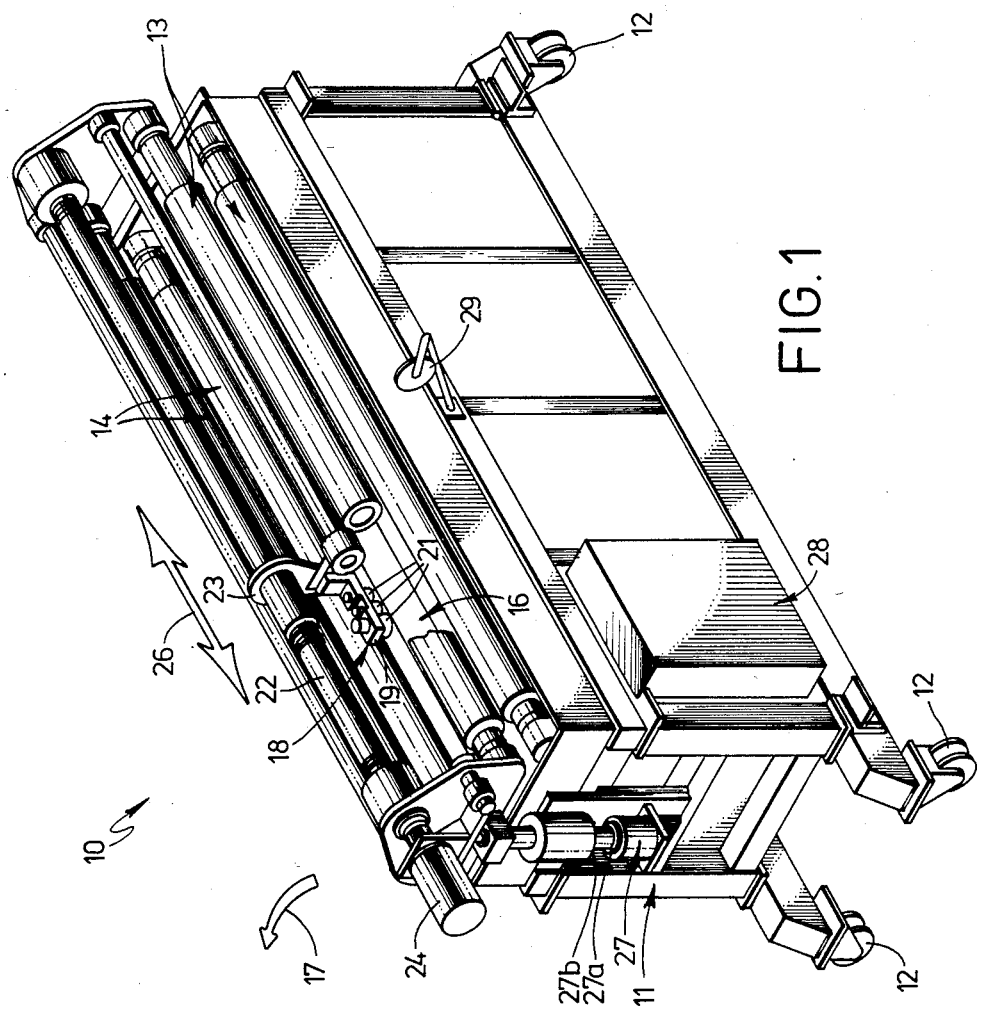
FIG. 1 illustrates a system for ultrasonically inspecting a continuous plastic sheet according to a presently preferred embodiment of the invention.

FIG. 1 illustrates an ultrasonic inspection system according to a presently preferred embodiment for inspecting multi-layer material such as coextruded plastic sheet for the presence and the thickness of the various layers thereof. The system is generally designated by reference numeral 10 and includes a support frame or table 11 which supports many of the components of the system. The table is supported on a plurality of "V" casters 12 to permit it to move on rails along with the rest of the production line. In particular, the unit is designed to be incorporated into the production line to receive coextruded plastic sheet directly from the coextrusion equipment and to inspect the plastic sheet as it is being made. The coextrusion equipment and the sheet itself are not illustrated in FIG. 1 for purposes of clarity.

Included on the table 11 are means for receiving and supporting a section of the sheet in position to be inspected. This means comprises a plurality of rollers including a first pair of upstream rollers 13, a second pair of downstream rollers 14, and an intermediate sheet guide roller 16 therebetween. A sheet moving from the coextrusion equipment toward the table in the direction indicated by arrow 17 will be fed between the first pair of rollers 13, over the sheet guide roller 16, and out of the unit through the second pair of rollers 14. A section of the sheet will be held relatively taut between the two pairs of rollers 13 and 14 to permit it to be inspected by a transducer means assembly generally indicated by reference numeral 18.

More particularly, transducer means assembly 18 comprises a mounting member 19 for supporting at least one transducer means 21 (three transducer means are illustrated in FIG. 1.) directly above the surface of the sheet section between the two pairs of rollers 13 and 14. The transducer means 21 will be described in detail hereinafter.

Mounting member 19 is attached to a drive screw 22 by a coupling 23; and the drive screw 22 is, in turn, driven by an indexing driver motor 24 mounted to one end thereof. The indexing driver motor 24 powers the drive screw which, in turn, moves the transducer means assembly 18 back and forth across the width of the sheet in the directions indicated by arrow 26. As the transducer means assembly is traversed across the sheet, the transducer means 21 will be energized to direct ultrasonic pulses into the sheet to be reflected from an interface therein to provide information regarding the presence or absence of any barrier layer within the sheet or of the thickness of the various layers.

By employing one transducer means 21, a given area of the sheet can be effectively inspected. If desired, a plurality of transducer means 21, each generating different frequency signals (for example, from above 0.5 MHz to above 25 MHz) can also be employed to allow a broader range of thickness gauging to be accomplished.

The plastic sheet is adapted to be driven through apparatus 10 in a continuous manner at a substantially constant velocity of, for example, about 120 inches per minute. Indexing motor 24 is adapted to drive the transducer means back and forth across the moving sheet to produce a zig-zag path of the transducer means relative to the surface of the sheet.

A cylinder 27, which may be hydraulically or pneumatically driven, is provided to move the drive screw 22 and the transducer assembly 18 mounted thereto, together with the upper rollers of roller pairs 13 and 14 toward and away from the sheet to properly position the transducer means relative to the sheet. Adjustable stops 27a and 27b (not shown) can be provided to position the transducer means at the desired fixed distance relative to the sheet surface. These stops also provide a means for maintaining the proper nip at the roller pairs.

The table 11 also supports the means for analyzing the reflected pulses returned to the transducer means from any interface within the sheet. This analyzing means and the system control is conveniently stored within a box 28 and will be described more fully hereinafter. In addition, the table includes linear length indicator 29 for use in correlating the location of points on the sheet that have been inspected by the apparatus.

FIGS. 2-5 illustrate one of the transducer means 21 employed in the system 10 of FIG. 1. As shown, the transducer means comprises a housing 31 of generally tubular shape that is open at both its top end 32 and its bottom or base end 33. An ultrasonic transducer 34, which may be of conventional type such as a piezoelectric or magnetostrictive transducer, extends into the housing through its top end 32 and is supported within the housing 31 such that the face 36 of the transducer will be spaced from the base end 33 of the housing as illustrated.

Housing 31 includes a relatively rigid housing portion 35 of metal or the like and an annular housing base portion 37 of relatively soft, flexible material such as a urethane elastomer or the like having a hardness of about 40-90 durometer and preferably about 40-50 durometer. The flexible base portion 37 is attached to rigid portion 35 and extends therefrom to define the base end 33 of the housing which is positioned in contact with the surface of a sheet 38 to be inspected. Annular portion 37 can be glued or otherwise affixed to rigid housing portion 35 in any convenient manner.

Housing 31 defines a chamber 41 between the face 36 of the ultrasonic transducer and the surface of sheet 38 to be inspected which is adapted to be filled with an interfacing fluid such as water to maintain a column of interfacing fluid between the face of the transducer and the surface of the sheet. Chamber 41 is kept filled with interfacing fluid at all times during an inspection operation from a source of interfacing fluid 42 (shown schematically in FIG. 2) coupled to the housing 31 through a fluid inlet 43 in the upper portion of the housing. The interfacing fluid may be provided to the housing by a pump 44 or by other means such as by pressurizing the source 42 and controlling the flow by a valve in place of pump 44. The level of fluid in the housing may be maintained by either a constant or periodic delivery of fluid from the source 42.

Figure 3:
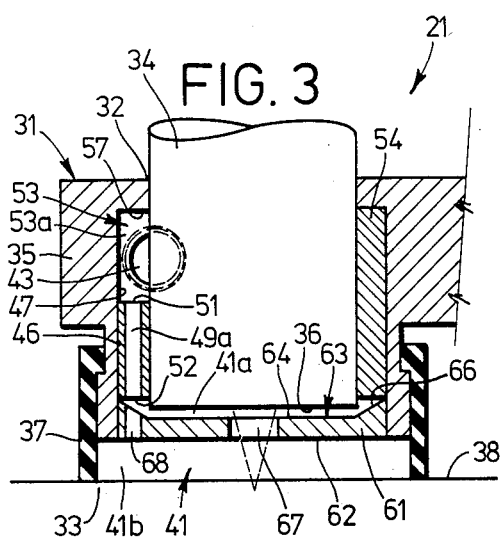
FIG. 3 is a cross-sectional view of the transducer means of FIG. 2 looking in the direction of arrows 3—3 in FIG. 2.
Figure 5:
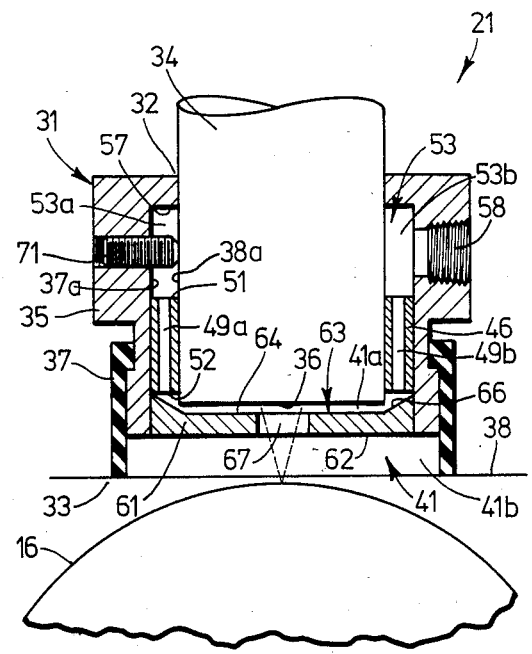
FIG. 5 is a cross-sectional view of the transducer means of FIG. 2 looking in the direction of arrows 5—5 in FIG. 2.

As best shown in FIGS. 3 and 5, an annular sleeve 46 is positioned within housing portion 35 and surround the lower portion of transducer 34. Sleeve 46 may be formed of plastic or metal and is mounted to the inner wall 47 of housing portion 35 and to the outer wall 48 of the transducer 34 in a substantially fluid-tight manner. As will be explained more fully hereinafter, sleeve 46 is provided with a plurality of passageways 49 substantially uniformly spaced around the circumference of the sleeve and extending from the top face 51 to the bottom face 52 of the sleeve.

Above the sleeve 46 and surrounding the transducer 34 an annular compartment 53 is formed by housing portion 35 and transducer 39. Compartment 53 is divided into first and second portions 53a and 53b, respectively, by a pair of blocking elements 54 and 56. Blocking elements 54 and 56 extend from the top face 51 of sleeve 46 to the inner face 57 of the top wall of the housing portion 35, and engage the walls 37a and 38a of the housing and the transducer in a fluid-tight manner to prevent any direct fluid communication between compartment portions 53a and 53b.

Fluid inlet 43 is coupled to compartment portion 53a, while compartment portion 53b is coupled to a fluid outlet 58 through which fluid is adapted to be discharged from the housing 31 to a reservoir or other fluid receiving means (not shown).

Figure 6:
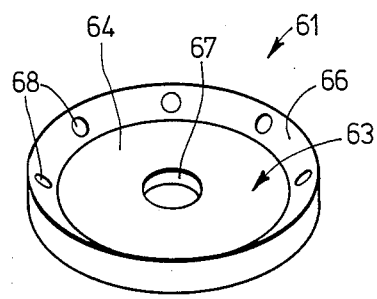
FIG. 6 is a perspective view of a component of the transducer means.

A disk-shaped element 61 is also positioned within housing portion 35 beneath the face 36 of the transducer 34. As best shown in FIGS. 3, 5 and 6, element 61 comprises a flat bottom surface 62 and a somewhat concave top surface 63. More particularly, top surface 63 includes a generally flat central portion 64 and peripheral portion 66 which is inclined inwardly and downwardly at an angle of approximately 30° from the outer edge of insert 61 to the central surface portion 64. Element 61 also includes a relatively large central aperture 67 and a plurality of smaller peripheral apertures 68 extending from the top surface 63 to the bottom surface 62 thereof.

In the presently preferred embodiment, element 61 is approximately 1⅜ inches in diameter while central surface portion 64 is about 1 5/16 inches in diameter. Central aperture 67 is about 5/16 inch in diameter while peripheral apertures 68 are about ⅛ inch in diameter. Element 61 may be constructed of plastic or metal or any other suitable material.

Element 61 divides chamber 41 into a first upper chamber portion 41a and a second lower chamber portion 41b. Upper chamber portion 41a is adjacent the face 36 of the transducer 34 and is relatively narrow in size, for example, (less than about ⅛ inch wide) while lower chamber portion 41b is adjacent the surface of sheet 38 and is somewhat larger, about ¼ inch or more wide.

As will be explained hereinafter, element 61 is adapted to function as a fluid directing means with its top surface directing interfacing fluid substantially transversely across the face 36 of the transducer 34 to prevent the entrapment of any bubbles between the face of the transducer and the surface of the sheet.

Figure 2:
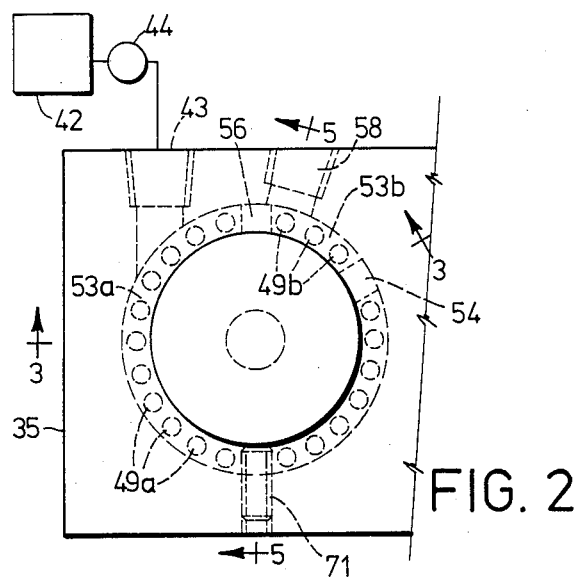
FIG. 2 is a top view of a transducer means utilized in the apparatus of FIG. 1.

As indicated above, sleeve 46 includes a plurality of passageways 49 extending therethrough. Passageways 49 include a first plurality of inlet passageways 49a connecting compartment portion 53a to upper chamber portion 41a, and a second plurality of outlet passageways 49b connecting chamber portion 41a to compartment portion 53b. As can be seen in FIG. 2, compartment portion 53a is much larger than compartment portion 53b and extends approximately 300° around the circumference of the transducer. Accordingly, there are many more inlet passageways 49a than outlet passageways 49b, and inlet passsageways 49a are substantially uniformly spaced approximately 300° around the circumference of the transducer.

In operation, transducer means 21 is positioned such that annular, flexible base portion 37 of housing 31 presses against the surface of sheet 38 to be inspected. Chamber 41 is then filled with an interfacing fluid through fluid inlet 43 from source 42. Upper chamber portion 41a receives fluid through inlet 43, compartment portion 53a, and the first plurality of inlet passageways 49a. Lower chamber portion 41b receives fluid from upper chamber portion 41a through apertures 67 and 68 in disk-shaped element 61.

The chamber 41 is maintained filled with fluid from source 42 such that face 36 of the transducer 34 will be completely enveloped and swept with interfacing fluid and a column of fluid will be maintained between the face of the transducer and the surface of sheet 38 being inspected at all times. Standard water main pressure, e.g., 40-50 psi, will operate effectively with the transducer system shown in FIGS. 2-6. The transducer 34 can then be energized to direct an ultrasonic pulse through the interfacing fluid in chamber portions 41a and 41b, through central aperture 67 in element 61 and into the sheet 38. Interfaces within the sheet will partially reflect the pulse echo back to the transducer which converts the echo back to an electrical signal which can then be processed and analyzed to provide information concerning the presence and thickness of layers within the sheet. As shown in FIG. 5, sheet guide roller 16 helps to support the sheet 38 and keep it flat against the transducer means 21.

As the transducer means 21 is moved back and forth across the sheet 38 by drive screw 22 (FIG. 1), the narrow column of interfacing fluid within chamber 41 will move along with it to provide the necessary interfacing medium between the transducer and sheet at all times.

Annular, flexible housing base portion 37 provides for a minimum amount of contact between the transducer means and the surface of the sheet 38 and, being quite soft, minimizes the risk of abrasion or other damage to the surface of the sheet. Base portion 37 also acts as a seal to help retain the fluid within the chamber 41. Any fluid that does leak out between the bottom of base portion 37 and the surface of sheet 38, however, will automatically be replenished from source 42.

Interfacing fluid flows into upper chamber portion 41a from compartment portion 53a through the plurality of inlet passageways 49a. Blocking elements 54 and 56, in addition to preventing direct fluid transfer from compartment portion 53a to compartment portion 53b, also function as dam members to help direct the fluid down into the passageways 49a.

Figure 4:
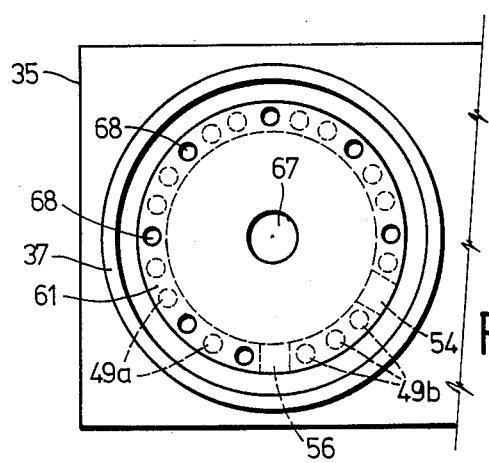
FIG. 4 is a bottom view of the transducer means of FIG. 2.

Fluid exiting from passageways 49a will enter into upper chamber portion 41a. A portion of this fluid will flow through peripheral apertures 68 in disk-shaped element 61 into lower chamber portion 41b to help maintain that portion filled with fluid. A substantial portion of the fluid, however, especially since apertures 68 are displaced from inlet passageways 49a as shown in FIG. 4, will flow inwardly as a result of the peripheral portion 66 on element 61 and the applied fluid pressure. This inwardly flowing fluid sweeps across the face 36 of transducer 34, and, in doing so, washes away any air bubbles that tend to attach themselves to the face of the transducer as a result of surface tension. Because inlet passageways 49a are positioned around approximately 300° of the circumference of the transducer face, fluid will flow across the entire extent of the transducer face, and air bubbles will be very effectively carried away from face 36.

Fluid flowing across face 36, together with any air bubbles carried thereby will be carried away either through central aperture 67 in disk-shaped element 61 or through the plurality of outlet passageways 49b in sleeve 46 into second compartment portion 53b and out of the housing through outlet 58.

With the present invention, therefore, the column of interfacing fluid between the face of the transducer and the surface of the sheet will be kept free of air bubbles that might affect the accuracy of the measurements by a fast moving stream of interfacing fluid thereacross. A flow rate across the face of the transducer as low as 0.01 gallon per minute is effecting to prevent entrapment of bubbles with the system shown in FIGS. 2-6; but flow rates of about 0.017 gallon per minute are more effective and are preferable; and the physical dimensions of the transducer housing system and the fluid pressure may be varied to obtain varied effective flow rates.

Rollers 13 and 14 (FIG. 1), in addition to supporting the sheet 38 in position to be inspected, also function as squeegee rollers to remove and contain any interfacing fluid which is left behind on the sheet. These rollers also keep the sheet in contact with the linear length indicator 29.

Figure 7:
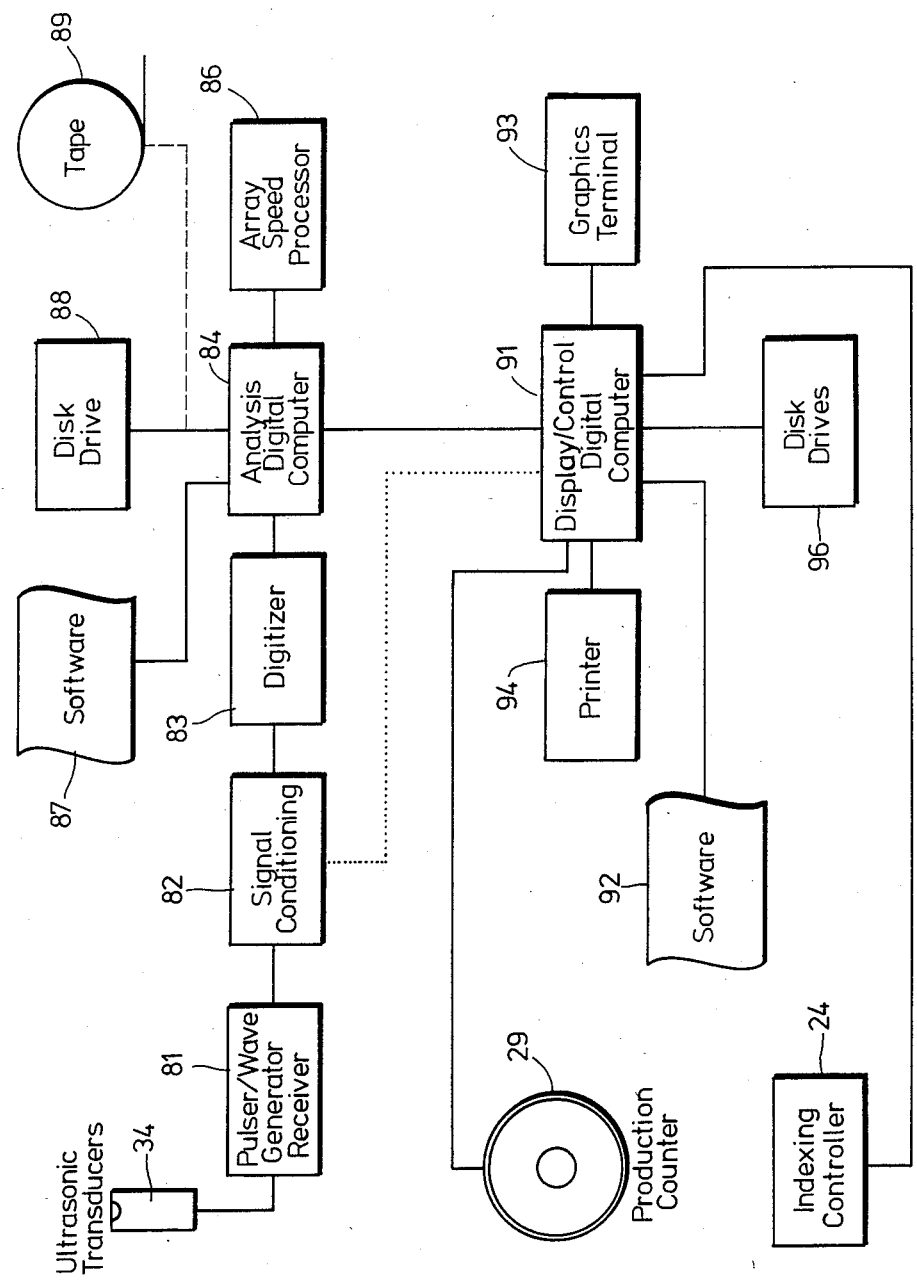
FIG. 7 is a block diagram of the electronic system of the ultrasonic inspection system of the present invention.

FIG. 7 is a block diagram of the electronic system for processing, analyzing, and displaying the ultrasonic pulse echoes reflected back to the transducer means 21 from interfaces within sheet 38. As indicated above, some of this structure is stored on table 11 within box 28 (FIG. 1). Initially, ultrasonic transducers are selected having the appropriate frequency for the particular sheet thickness being inspected and are mounted within each transducer means 21, and locked in position by locking screw 71 (FIG. 5).

Once activated, a pulser/receiver 81 associated with each transducer means will generate an electrical pulse exciting the ultrasonic transducer 34 therein; and the pulse from the transducer will pass through the column of interfacing liquid in chamber 41 and into the sheet 38 to be reflected from an interface therein. The reflected echo will return to the transducer, be converted back to an electrical signal, and directed back to the pulser/receiver 81. Pulser/receiver 81 is basically a wave generator/amplifier. The received signal is passed through a signal conditioner 82 which amplifies and filters the signal in accordance with known procedures. The filtered signal is then passed to a digitizer 83, which converts the wave into numerical form for subsequent analysis.

Once in numerical form, the information is analyzed for the presence and thickness of the layers in the analysis digital computer 84. An array processor 86, which may be obtained from Analogic, may be provided to perform dedicated mathematical calculations at high speed and may be used to enhance the analysis rate. The array processor/analysis digital computer combination functions by means of a number of software packages illustrated generally by reference numeral 87 with a disk drive 88 and tape system 89 as input and storage vehicles.

After being analyzed, the processed data may then transmitted to a display/control digital computer 91 of the type made by Intel. By means of appropriate software 92, the information is then statistically analyzed for final output. Output takes the form of visual display on a graphics terminal 93, and hard copy for management control by means of a printer 94. The display/control digital computer 91 has a disk drive 96 and also handles all control functions such as reversing the indexer motor 24 at the end of each completed stroke, and monitoring the current number of feet of extruded sheet counted by linear length indicator 29. Although the use of an array processor 86 and a display/control digital computer 91 are described herein, these components are not essential in the general application of the invention and their functions can be incorporated into the analysis digital computer 84.

While what has been described constitutes a presently most preferred embodiment of the invention, it should be understood that the invention could take various other forms. For example, although the system has primarily been described for use in inspecting coextruded plastic sheet, it could also be employed to inspect or test other types of articles. Accordingly, it should be understood that the invention should be limited only insofar as is required by the scope of the following claims.

We claim:

1. Acoustic inspection apparatus comprising:
    an acoustic transducer having a transducer face;
    means for supporting said transducer in spaced relationship with respect to an article to be inspected and for defining a fluid chamber between the face of said transducer and the article to be inspected;
    means for supplying an interfacing fluid to said fluid chamber;
    fluid directing means positioned within said chamber between the face of said transducer and the article to be inspected, said fluid directing means including a surface for directing said interfacing fluid substantially transversely across the face of said transducer from at least one peripheral location; and
    means located above said fluid-directing means for removing interfacing fluid and any air bubbles carried thereby from said chamber.

2. Apparatus as recited in claim 1 wherein said means for supplying interfacing fluid comprises means for supplying interfacing fluid to said chamber at a plurality of peripheral locations around the face of said transducer, and wherein said surface directs the interfacing fluid substantially transversely across the face of said transducer from said plurality of peripheral locations.

3. Apparatus as recited in claim 2 wherein said means for supplying interfacing fluid to said chamber at a plurality of locations comprises an annular sleeve surrounding said transducer, said annular sleeve having a plurality of passageways extending therethrough, and wherein said supply means further includes a source of interfacing fluid, said plurality of passageways receiving interfacing fluid from said source and supplying said interfacing fluid to said chamber.

4. Apparatus as recited in claim 1 wherein said fluid directing means comprises a generally disk-shaped element positioned within said chamber and defining a first chamber portion adjacent the face of said transducer and a second chamber portion adjacent said article to be inspected, and wherein said surface for directing interfacing fluid substantially transversely across the face of said transducer is on the upper surface of the disk-shaped element.

5. Apparatus as recited in claim 4 wherein said generally disk-shaped element includes a central portion and a peripheral portion, said peripheral portion being inclined downwardly toward said central portion and defining a portion of said surface for directing interfacing fluid substantially transversely across the face of said transducer.

6. Apparatus as recited in claim 5 wherein said central portion of said disk-shaped element further includes a central aperture extending therethrough for permitting acoustic energy to travel from the face of said transducer through said interfacing fluid in said chamber into said article to be inspected.

7. Apparatus as recited in claim 6 wherein said means for supplying interfacing fluid to said chamber comprises an annular sleeve surrounding said transducer, said annular sleeve having a first plurality of passageways extending therethrough, said first plurality of passageways being spaced around at least a substantial portion of the circumference of said transducer for directing interfacing fluid through said passageways into said first chamber portion to be directed substantially transversely across the face of said transducer from a plurality of peripheral locations by said peripheral portion of said disk-shaped element.

8. Apparatus as recited in claim 7 wherein said interfacing fluid supply means includes a fluid inlet and wherein said apparatus further includes a source of interfacing fluid coupled to said fluid inlet for supplying interfacing fluid to said first plurality of passageways to be directed into said first chamber portion therethrough.

9. Apparatus as recited in claim 8 wherein said disk-shaped element further includes a plurality of apertures extending therethrough around the peripheral portion of said disk-shaped element for supplying interfacing fluid to said second chamber portion for maintaining interfacing fluid therein.

10. Apparatus as recited in claim 8 wherein said fluid-removing means comprises fluid outlet means and wherein said annular sleeve further includes a second plurality of passageways for directing interfacing fluid from said first chamber portion to said fluid outlet means for withdrawing interfacing fluid and any air bubbles carried thereby from said first chamber portion.

11. Apparatus as recited in claim 10 wherein said support means further includes an annular compartment above said annular sleeve, said annular compartment including a first compartment portion for receiving interfacing fluid from said fluid inlet and a second compartment portion for receiving interfacing fluid from said second plurality of passageways in said annular sleeve to be directed to said fluid outlet, and wherein said compartment further includes blocking means for preventing direct transfer of said interfacing fluid from said first compartment portion to said second compartment portion and for directing said interfacing fluid into said first plurality of passageways in said annular sleeve.

12. Apparatus as recited in claim 1 wherein said support means includes a flexible base portion adapted to be positioned in contact with said article to be inspected.

13. Apparatus as recited in claim 1 and further including drive means for causing relative transverse movement between said article to be inspected and said support means, and said acoustic transducer and said interfacing fluid maintained by said support means.

14. Apparatus as recited in claim 1 wherein said transducer comprises an ultrasonic transducer.

15. Apparatus as recited in claim 1 wherein said article to be inspected comprises a coextruded plastic sheet.

16. Ultrasonic inspection apparatus comprising:
    a housing open at one end thereof, said open end of said housing being adapted to be positioned in contact with the surface of an article to be inspected;
    an ultrasonic transducer positioned within said housing with the face of said transducer being spaced from the open end of said housing, said housing defining an open-ended chamber between the face of said transducer and the surface of said article to be inspected;
    a fluid inlet in said housing connected to a source of interfacing fluid;
    a fluid outlet in said housing for discharging interfacing fluid from said housing;
    means for supplying interfacing fluid from said fluid inlet to said chamber, said fluid supplying means including first passageway means for supplying interfacing fluid to said chamber from a plurality of peripheral locations around the face of said transducer;

fluid directing means positioned within said chamber between the face of said transducer and the surface of the article to be inspected, said fluid-directing means including a surface for directing interfacing fluid substantially transvesely across the face of said transducer from said plurality of peripheral locations; and second passageway means for directing interfacing fluid and any air bubbles carried thereby from said chamber to said fluid outlet for removing air bubbles from within said chamber.

17. Apparatus for inspecting a sheet being continuously fed through said apparatus, comprising:

roller means continuously feeding said sheet longitudinally through said apparatus and for supporting at least a section of said sheet in position to be inspected;

means for supporting at least one ultrasonic transducer means in contact with the surface of said sheet, each of said ultrasonic transducer means including:

a housing open at one end thereof, said open end of said housing being adapted to be positioned in contact with said surface of said sheet and including an annular flexible base portion in direct contact with the surface of said sheet; and an ultrasonic transducer positioned within said housing with the face thereof being spaced from the open end of said housing to define a chamber between the face of said transducer and said surface of said sheet which is adapted to be filled with an interfacing medium, said chamber including a surface to direct said interfacing medium across the face of said transducer from a peripheral location;

means for exciting said ultrasonic transducer for sending ultrasonic signals through said interfacing medium into said sheet, said ultrasonic transducer providing means for receiving ultrasonic signals reflected from said sheet;

means for analyzing said received ultrasonic signals; and drive means for moving said transducer means transversely across said sheet for inspecting different areas of said sheet.

18. Apparatus as recited in claim 17 wherein said drive means moves said at least one transducer means transversely from position to position across the surface of said sheet.

19. Apparatus as recited in claim 17 wherein at least some of said plurality of roller means comprise squeegee roller means for removing and containing any interfacing fluid left on said sheet by said at least one transducer means.

20. Apparatus as recited in claim 17 wherein said at least one transducer means comprises a plurality of transducer means.

21. Apparatus as recited in claim 17 wherein said sheet comprises coextruded plastic sheet being continuously fed from a production line.

22. Acoustic inspection apparatus comprising:

an acoustic transducer having a transducer face;

means for supporting said transducer in closely spaced relationshp with respect to an article to be inspected and for defining a chamber between the face of said transducer and said article to be inspected, said chamber being adapted to contain an interfacing fluid;

means for supplying an interfacing fluid to said chamber; and fluid-directing means positioned within said chamber adjacent the face of said transducer to divide said chamber into a first, narrow chamber portion adjacent the face of said transducer, and a second chamber portion adjacent said article to be inspected, said fluid-directing means including at least one surface for creating a flow of interfacing fluid substantially transversely across said first, narrow chamber portion and the face of said transducer when supplied with fluid from said fluid supply means and for removing air bubbles from adjacent said face of said transducer.

23. Apparatus as recited in claim 22 wherein said fluid-directing means comprises a generally disk-shaped element, said disk-shaped element having peripheral surfaces for directing said interfacing fluid substantially transversely across said first narrow chamber portion.

24. Apparatus as recited in claim 23 wherein said peripheral surfaces comprise inclined surfaces.

25. Apparatus as recited in claim 24 wherein said fluid-supplying means comprises means for supplying interfacing fluid to said chamber at a plurality of peripheral locations around the face of said transducer, and wherein said peripheral surfaces comprise an annular peripheral surface for directing said interfacing fluid substantially transversely across said first, narrow chamber portion from said plurality of peripheral locations.

* * * * *

UNITED STATES PATENT AND TRADEMARK OFFICE
CERTIFICATE OF CORRECTION

PATENT NO. : 4,587,849

DATED : May 13, 1986

INVENTOR(S) : R. Michael Gross and Earl L. Lowe

It is certified that error appears in the above-identified patent and that said Letters Patent is hereby corrected as shown below:

At [75], Inventor, add --Earl L. Lowe--

In col. 5, line 48, delete "surround", and insert --surrounds-- therefor.

In col. 8, line 46, after "then", insert --be--.

In col. 11, line 8 (claim 16, line 26), delete "transvesely" and insert --transversely-- therefor.

In col. 12, line 17 (claim 22, line 4), delete "relationshp" and insert --relationship-- therefor.

Signed and Sealed this

Twenty-eighth Day of October, 1986

[SEAL]

Attest:

DONALD J. QUIGG

Attesting Officer     Commissioner of Patents and Trademarks